United States Patent
Roch et al.

(10) Patent No.: US 6,911,524 B1
(45) Date of Patent: Jun. 28, 2005

(54) ANTIMICROBIAL PEPTIDES DERIVED FROM MOLLUSKS

(75) Inventors: Philippe Roch, Montpellier (FR); Guillaume Mitta, Montpellier (FR); Florence Hubert, Montpellier (FR); Thierry Noel, Clapiers (FR)

(73) Assignees: Centre National de la Recherche Scientifique, Paris Cedex (FR); Institute Francais de la Recherche pour l'Exploitationde de la Mer (Ifremer), Issey-les-Moulineaux Cedex (FR)

( * ) Notice: Subject to any disclaimer, the term of this patent is extended or adjusted under 35 U.S.C. 154(b) by 120 days.

(21) Appl. No.: 10/030,231

(22) PCT Filed: Jul. 7, 2000

(86) PCT No.: PCT/FR00/01975

§ 371 (c)(1),
(2), (4) Date: Jun. 20, 2002

(87) PCT Pub. No.: WO01/04294

PCT Pub. Date: Jan. 18, 2001

(30) Foreign Application Priority Data

Jul. 8, 1999 (FR) .............................. 99 08858

(51) Int. Cl.[7] .................. A61K 38/00; A61K 35/56; C07K 14/00; C07K 16/00; C07K 17/00; C07K 2/00; C07K 4/00; C07K 5/00; C07K 7/00; C07K 1/00

(52) U.S. Cl. ................ 530/300; 530/324; 530/350; 424/547

(58) Field of Search ............................... 530/300, 324, 530/350; 424/547

(56) References Cited

U.S. PATENT DOCUMENTS 6,692,747 B2 * 2/2004 Kim et al. ............... 424/184.1
2004/0029802 A1 * 2/2004 Mansfield et al. ............ 514/12

FOREIGN PATENT DOCUMENTS

EP  0 349 451 A    1/1990
FR     2796072 A1 * 1/2001 ......... C07K/14/435
WO  WO 01/04294 A1 * 1/2001 ........... C12N/15/12

OTHER PUBLICATIONS

Mitta et al, Dev. Comp. Immunol., Jun. 2000, 24/4:381–393 Abstract Only.*
Zhang et al, Dev. Comp. Immunol., Jun. 2003, 27/6–7:499–503 Abstract Only.*
Mitta et al, Developmental and Comparative Immunology, Jun. 2000, 24:381–393.*
Mitta et al, Developmental and Comparative Immunology, 2000, 24:S1:S20 (meeting abstract).*
Mitta et al, J. Biological Chemistry, Apr. 2000, 275/17:12954–12962.*
Yang et al, Biochemistry, 2000, 39:14436–14447.*
Mitta et al, FEBS Letters, Dec. 2000, 486:185–190.*
Mitta et al, J. Cell Science, 2000, 113:2759–2769.*
Romestand et al, Eur. J. Biochem., Jul. 2003, 270/13:2805–2813.*
Kaneko et al., "Sequence analysis of the genome of the unicellular cyanobacterium Synechocystis sp. PCC6803." EMBL Sequence Database. Oct. 4, 1995.
Maurice Charlet et al.: "Isolation of Several Cysteine–Rich Antimicrobial Peptides From the Blood of a Mollusc, *Mytilus edulis*", The Journal of Bilogical Chemistry, Sep. 6, 1996, vol. 271, No. 36, pp. 21808–21813.
Guillaume Mitta et al., "Myticin, A Novel Cysteine–Rich Antimicrobial Peptide Isolated From Haemocytes and Plasma of the Mussel *Mytilus Galloprovincialis*." Eur. J. Biochem, vol. 265, Oct. 1999, pp. 71–78.

* cited by examiner

*Primary Examiner*—N. M. Minnifield
(74) *Attorney, Agent, or Firm*—Morgan, Lewis & Bockius, LLP

(57) ABSTRACT

The invention concerns an antimicrobial peptide, called myticin, characterised in that it can be obtained from a bivalve mollusc shellfish, and its molecular mass is about 4.5 kDa; its pI is about 8.7; it comprises 8 cystein radicals. The invention also concerns its preparation and its uses. The invention further concerns a nucleic acid coding for said peptide.

3 Claims, No Drawings

ANTIMICROBIAL PEPTIDES DERIVED FROM MOLLUSKS

The invention relates to novel antimicrobial peptides produced by mollusks.

Polypeptides possessing antimicrobial properties are produced by a large variety of species (animal or plant species), in which they contribute to nonspecific mechanisms of defense against infections.

In the case of bivalve mollusks, to date, in *Mytilus galloprovincialis*, a peptide named MGD-1 has been identified, which is related to insect defensins [HUBERT et al., Eur. J. Biochem., 240, 302–306, (1996)]; peptides of the defensin family have also been demonstrated in *Mytilus edulis*, as have peptides named "mytilins" [CHARLET et al., J. Biol. Chem., 271, 21808–21813, (1996)].

The inventors have now demonstrated novel antimicrobial peptides produced by *Mytilus galloprovincialis*, which are different from the MGD1 defensins and form the previously known mytilins.

A subject of the present invention is antimicrobial peptides, hereinafter named: "myticins", which have the following characteristics:

their molecular mass is approximately 4.5 kDa;

their pI is approximately 8.7;

they comprise 8 cysteine residues.

According to a preferred embodiment of an antimicrobial peptide in accordance with the invention, it comprises the following sequence (I) (1-letter code):

$HX_1HX_2CTSYX_3CX_4KFCGTAX_5CTX_6YX_7CRX_8LHX_9GKX_{10}CX_{11}CX_{12}HCSR$ (I)

in which: $X_1$=P or S, $X_2$=V or A, $X_3$=Y or W, $X_4$=S or G, $X_5$=S or G, $X_6$=R or H, $X_7$=G or L, $X_8$=N or V, $X_9$=R or P, $X_{10}$=L or M, $X_{11}$=F or A, and $X_{12}$=L or V. (SEQ ID NO: 5).

in which: $X_1$=P or S, $X_2$=V or A, $X_3$=Y or W, $X_4$=S or G, $X_5$=S or G, $X_6$=R or H, $X_7$=G or L, $X_8$=N or V, $X_9$=R or P, $X_{10}$=L or M, $X_{11}$=F or A, and $X_{12}$=L or H.

Advantageously, a peptide in accordance with the invention comprises one of the following sequences (Ia) or (Ib) (1-letter code):

HSHACTSYWCGKFCGTASCTHYLCRVLHPGKMC
ACVHCSR         (Ia) (SEQ ID NO:6)

HPHVCTSYYCSKFCGTAGCTRYGCRNLHRG
KLCFCLHCSR      (Ib) (SEQ ID NO:7).

The sequences (Ia) and (Ib) represent the mature forms, isolated from the hemolymph of *Mytilus galloprovincialis*, of 2 myticins named Myticin a and Myticin b, the cDNAs of which have also been cloned by the inventors. By way of illustration of the subject of the present invention, the characteristics of Myticin a and Myticin b are more specifically indicated below.

The cDNA sequence and the polypeptide sequence of Myticin a are represented in the attached sequence listing, under the numbers SEQ ID NO: 1 and SEQ ID NO: 2. The cDNA sequence and the polypeptide sequence of Myticin b are represented in the attached sequence listing, under the numbers SEQ ID NO: 3 and SEQ ID NO: 4.

The 40 amino acid active peptide, corresponding to the sequence (I), and more particularly to one of the sequences (Ia) and (Ib), is flanked by a 20 amino acid signal sequence and by a 36 amino acid C-terminal peptide. The signal sequence is thought to enable the addressing of the translation product toward the endoplasmic reticulum. The C-terminal peptide would then enable addressing toward the cytoplasmic granules in which the myticins are stored in mature form, and/or protection of the cell against possible cytolytic activity of the mature peptide.

The molecular mass of the mature form of Myticin a is 4438 Da; the molecular mass of the mature form of Myticin b is 4562 Da.

Myticins exhibit no significant homology with the known antimicrobial peptides in the prior art, and define a novel group of antimicrobial peptides.

Myticins may be obtained by extraction from the mollusks which produce them, by peptide synthesis or, advantageously, by genetic engineering, expressing at least one nucleic acid sequence encoding a myticin, in a suitable host cell.

The present invention also encompasses nucleic acids comprising a sequence encoding a myticin, as defined above.

Nucleic acids in accordance with the invention may be obtained by screening nucleic acid libraries using oligonucleotides derived from the sequences SEQ ID NO: 1 or SEQ ID NO: 3, or from the sequences complementary thereto. The oligonucleotides which can be used for this purpose are also part of the subject of the present invention; advantageously, these oligonucleotides comprise at least 15 bp, and preferably at least 20 bp, of the coding region of one of the sequences SEQ ID NO: 1 or SEQ ID NO: 3, or of the sequence complementary thereto.

The nucleic acids in accordance with the invention also encompass the expression cassettes comprising at least one nucleic acid sequence encoding a myticin, placed under the transcriptional control of a suitable promoter.

The term "suitable promoter" is intended to mean any promoter which is functional in the host cell intended to harbor the expression cassette. It may be a constitutive promoter or an inducible promoter; it may also be, when the cassette is intended for the expression of a myticin in an animal or a plant, a tissue-specific promoter.

An expression cassette in accordance with the invention may also comprise at least one sequence encoding a suitable addressing sequence; said addressing sequence may be chosen from those which are naturally associated with myticins, such as the signal sequences and/or the C-terminal sequences associated with the Myticin a and Myticin b isoforms described above; it is also possible to choose one or more heterologous addressing sequences which are functional in a given host cell: they may in particular be sequences which allow the addressing of a myticin toward a given cellular compartment, or its secretion into the culture medium.

A subject of the invention is also:

recombinant vectors, characterized in that they comprise at least one nucleic acid sequence in accordance with the invention, encoding a myticin, and, in particular, vectors comprising an expression cassette as defined above.

prokaryotic or eukaryotic cells transformed with at least one nucleic acid sequence in accordance with the invention. They may be cells in culture or cells which form part of an animal or plant multicellular organism. The nucleic acid sequence in accordance with the invention present in a transformed cell may be either incorporated into the chromosomal DNA of said cell, or be carried by an extrachromosomal vector.

A subject of the invention is also a method for producing a myticin, characterized in that it comprises expressing said myticin in at least one transformed cell in accordance with the invention.

The myticins in accordance with the invention may be expressed in cultures of cells transformed using techniques similar to those used for antimicrobial peptides of the prior art, for example in insect cells, as. described by HELLERS et al. [Eur. J. Biochem. 199, pp. 435–439, (1991)] for cecropins, or in yeast, as described by REICHHART et al. [Invertebrate Reproduction and Development, 21, pp. 15–24, (1992)].

They may also be expressed in transgenic animals or plants, in order to increase the resistance thereof to infections, as described, for example, by JAYNES et al. [Plant Science, 89, pp. 43–53 (1993)] in the case of peptides analogous to cecropin B, expressed in transgenic tobacco plants, or by NORELLI et al. [Euphytica, 77, pp. 123–128 (1994)] for transgenic apple tree plants expressing the attacin-E gene.

The myticins can be used in particular for producing anti-infectious, for example antibacterial or fungicidal, products, and in particular medicinal products.

Such products are applied for preventing and treating various microbial diseases, in very varied sectors, in particular in the domains of health and of agriculture, and in that of aquaculture, in order to limit the development of infectious diseases in breeding stocks.

The present invention will be more clearly understood from the further description which follows, which refers to examples of purification and of characterization of the myticins.

EXAMPLE 1

Isolation of Antimicrobial Peptides from the Hemolymph of *Mytilus galloprovincialis*

Preparation of the Hemolymph Fractions

An immune reaction is induced in adult mussels (*Mytilus galloprovincialis*) according to the following protocol: the liquid is removed from the shell, and 100 µl of a suspension of bacteria ($10^9$ bacteria/ml) or of fungi (suspension of hyphae at 1 OD at 600 nm), heat-killed beforehand, are injected into the adductor muscle. The hemolymph (approximately 0.5 ml/animal) is removed from the posterior adductor muscle using a syringe, in the presence of one volume of MAS (Modified Alsevier Solution) anti-aggregating buffer, and immediately centrifuged at 800 g for 15 min at 4° C. Aprotinin (5 µg/ml) is added to the supernatant, corresponding to the plasmatic fraction, which is frozen (−80° C.) until use, and the cell pellet is dried and stored at −80° C. until use.

Purification of Myticins

Plasmatic fraction: The plasma is diluted (1:1 v/v) in water sterilized by ultrafiltration (MilliQ), to which 0.1% of trifluoroacetic acid has been added. The pH is brought to 3.9 by adding 1 M HCl, with stirring, in an iced water bath for 30 min. After centrifugation (10 000 g, 20 min, 4° C.), the supernatant is harvested and kept at 4° C. until use.

Hemocytes: After thawing, the hemocyte pellet is resuspended in 5 volumes of 50 mM Tris buffer, pH 8.7, containing 50 mM NaCl, and homogenized. After centrifugation (10 000 g, 20 min, 4° C.), the pellet containing the cellular organelles is taken up in 3 volumes of 2 M acetic acid and treated by sonication (3×30 s) in an iced water bath. After removal of the debris by centrifugation (10 000 g, 20 min, 4° C.), the acid extract is stored at 4° C. until use.

HPLC Purification

The plasmatic fraction or the acid extracts of hemocytes are loaded onto SEP-PAK C18 VAC columns (WATERS ASSOCIATES) pre-equilibrated with acidified (0.05% trifluoroacetic acid) water. After washing with the acidified water, 2 successive elutions are carried out with solutions of acetonitrile at 10% and 40% in acidified (0.05% trifluoroacetic acid) water. The fractions obtained are lyophilized and reconstituted with ultrafiltered water, before being subjected to reverse-phase HPLC chromatography.

All the HPLC purification steps were carried out on a BECKMAN GOLD HPLC system equipped with a BECKMAN 168 detector. The elution is monitored by measuring UV absorption at 225 nm.

Step 1: The fractions eluted on SEP-PAK at 40% of acetonitrile are loaded onto a SEPHASIL C18 reverse-phase HPLC column (250 mm×4.1 mm) (PHARMACIA). Elution is carried out with a linear gradient of 5 to 50% of acetonitrile in the acidified water, for 90 min at a flow rate of 0.9 ml/min. The fractions corresponding to the absorbence peaks are collected in polypropylene tubes (MICROSORB, 75×12 mm, NUNC IMMUNOTUBES), dried under vacuum and reconstituted with ultrafiltered water, prior to testing their antimicrobial activity.

Step 2: The active fractions recovered at the end of step 1 are loaded onto a SEPHASIL C8 reverse-phase HPLC column (250 mm×4.1 mm) (PHARMACIA). The elution is carried out, at a flow rate of 0.9 ml/min, with a linear gradient of 20 to 30% of acetonitrile in the acidified water for 40 min.

Step 3: The active fractions recovered at the end of step 2 are loaded onto a SEPHASIL C18 column (250 mm×4.1 mm) (PHARMACIA), using the biphasic gradient described in step 2, at a flow rate of 0.9 ml/min.

Step 4: The final purification step is carried out on a DELTA PAK HPI C18 reverse-phase column (2×150 mm) (WATERS ASSOCIATES), using the biphasic gradient described in step 2, at a flow rate of 0.3 ml/min.

EXAMPLE 2

Antimicrobial Activity of the Peptides Obtained

Microorganisms Used:

The list of the microorganisms used to determine the antimicrobial activities of Myticin a and of Myticin b is indicated below, in table 1.

Antimicrobial Assay and Determination of the MBC:

The minimum bacterial concentration (MBC) of the peptides was determined according to the protocol described by HANCOCK et al.

A series of successive doubling dilutions of the peptides, in an aqueous solution containing 0.01% of acetic acid and 0.2% of bovine serum albumin (BSA), is prepared.

10 µl aliquots of each dilution are incubated in sterile 96-well polypropylene microtitration plates, in the presence of 100 µl of bacterial suspension at a starting optical density of $A_{600}$=0.001, in MUELLER HINTON BROTH liquid medium. The incubation is carried out for 18 h at 37° C. with stirring, except in the case of the marine bacteria, for which the incubation is carried out 25° C. The MBC is determined by plating out, onto solid MUELLER HINTON AGAR medium, the content of the wells corresponding to the first 3 dilutions for which no bacterial growth is observed, and incubating at 37° C. for 18 hours. The lowest concentration of peptide which prevents any residual formation of colonies corresponds to the MBC.

Antifungal Activity:

The antifungal activity was determined by calculating the MIC (minimum inhibitory concentration) in a test of inhibition of *Fusarium oxysporum* growth in liquid phase, according to the protocol described by FELHBAUM et al. [J. Biol. Chem., 269: 33159–63, (1994)].

A series of successive doubling dilutions of the peptides is prepared as indicated above for determining the antibacterial activity.

80 μl of spores suspended (final concentration $10^4$ spores/ml) in Potato Dextrose Broth medium (DIFCO) are added to 10 μl of peptide solution in sterile 96-well polypropylene microtitration plates. The final volume is adjusted to 100 μl by adding water. The growth inhibition is determined after incubation for 24 hours at 25° C. in the dark, by observation under a microscope and measurement of the increase in the $OD_{600}$. The value of the MIC corresponds to a range (a–b) of peptide concentrations, in which (a) represents the highest concentration at which growth is observed, and (b) represents the lowest concentration which induces 100% growth inhibition.

Antiprotozoan Activity:

The oyster-parasite protozoan *Perkinsus marinus* is cultured in DMEM medium (GIBCO), according to the protocol described by GAUTHIER and VASTA [J. Invertebr. Pathol., 66, 156–168, (1995)].

10 μM of purified peptide are added to $4\times10^4$ *P. marinus*, in seawater (final volume 20 μl). The mixture is incubated for 1 hour at room temperature. The viability of the parasites is estimated by staining with acridine orange and with ethidium bromide, as described by MORVAN et al. [J. Invertebr. Pathol., 69, 177–82 (1997)]. The maximum viability is evaluated, as a positive control, in samples to which the peptide has not been added.

The results of the various experiments carried out, for the Myticin a and Myticin b peptides, are illustrated by table 1 below; the biological activities are expressed in μM.

TABLE 1

|  | Myticin a | Myticin b |
| --- | --- | --- |
| BACTERIA Gram-positive |  |  |
| *Micrococcus luteus* | 2.25–4.5 | 1–2 |
| *Bacillus megaterium* | 2.25–4.5 | 1–2 |
| *Staphylococcus aureus* | >20 | >20 |
| *Listeria monocytogenes* | >20 | >20 |
| *Aerococcus viridans* | 4.5–9 | 2–4 |
| *Enterococcus faecalis* | >20 | N.D. |
| Gram-negative |  |  |
| *Escherichia coli* D31 | >20 | 10–20 |
| *Salmonella newport* | >20 | >20 |
| *S. typhimurium* | >20 | >20 |
| *Brucella suis* | >20 | >20 |
| *Pseudomonas aeruginosa* | >20 | N.D. |
| *Enteromonas aerogenes* | >20 | N.D. |

TABLE 1-continued

|  | Myticin a | Myticin b |
| --- | --- | --- |
| *Vibrio alginolyticus* | >20 | >20 |
| *V. vulnificus* | >20 | >20 |
| *V. splendidus* | >20 | >20 |
| FUNGI |  |  |
| *Fusarium oxysporum* | >20 | 5–10 |
| OYSTER-PARASITE PROTOZOAN |  |  |
| *Perkinsus marinus* | >20 | >20 |

N.D.: not determined

These results show that the 2 peptides are active, in particular on *Micrococcus luteus*; the Myticin b peptide also appears to be more active than the Myticin a peptide on *Micrococcus luteus*, *Escherichia coli* and *Fusarium oxysporum*.

EXAMPLE 3

Myticin Peptide cDNA Cloning

A cDNA library was constructed in the ZAP EXPRESS vector (STRATAGENE) using total poly(A)$^+$ RNAs from adult mussel hemocytes. A DNA probe representing 83 bp of the Myticin a cDNA was constructed using the PCR SCRIPT Amp (SK+) cloning kit (STRATAGENE), and labeled by random priming using the READY-TO-GO DNA labeling kit (PHARMACIA), and used to screen the DNA library transferred onto HYBOND-N membranes (AMERSHAM). Hybridizations at high stringency were carried out overnight at 65° C. in 5× Denhardt's solution, 5×SSPE, 0.1% SDS, 100 μg/ml of salmon sperm DNA. The filters, rinsed beforehand at 65° C in 0.5×SSC solution containing 0.1% SDS, were autoradiographed. A secondary screening was carried out in order to purify the positive clones. The phagemids were obtained by in vivo excision and both of their strands were sequenced.

110 positive clones were obtained. Among these clones, 4 were sequenced, and correspond to the Myticin a and Myticin b peptides.

In both cases, the amino acid sequence deduced from the open reading frame begins with a 20 amino acid signal peptide; this signal peptide is directly followed, at its C-terminal end, by a 40 amino acid peptide beginning with a histidine residue, which corresponds to the active form of the peptide; this active peptide is followed by a 36 amino acid C-terminal extension.

What is claimed is:

1. An isolated antimicrobial peptide, named myticin, from a bivalve mollusk, having a calculated molecular weight of approximately 4.5 kDa; a pI of approximately 8.7; and 8 cysteine residues; wherein said peptide further comprises the following sequence:

$HX_1HX_2CTSYX_3CX_4KFCGTAX_5CTX_6YX_7CRX_8LHX_9GKX_{10}CX_{11}CX_{12}HCSR$ in which: $X_1$=P or S, $X_2$=V or A, $X_3$=Y or W, $X_4$=S or G, $X_5$=S or G, $X_6$=R or H, $X_7$=G or L, $X_8$=N or V, $X_9$=R or P, $X_{10}$=L or M, $X_{11}$=F or A, and $X_{12}$=L or V (SEQ ID NO: 5).

2. The peptide of claim 1, chosen from the group consisting of:

a peptide comprising the following sequence (Ia):

HSHACTSYWCGKFCGTASCTHYLCRVLHP
GKMCACVHCSR (Ia) (SEQ ID NO: 6)

a peptide comprising the following sequence (Ib):

HPHVCTSYYCSKFCGTAGCTRYGCRNLHR
GKLCFCLHCSR (Ib) (SEQ ID NO: 7).

3. An isolated peptide comprising the amino acid sequence of SEQ ID NO: 6.

* * * * *

SEQUENCE LISTING

<160> NUMBER OF SEQ ID NOS: 7

<210> SEQ ID NO 1
<211> LENGTH: 663
<212> TYPE: DNA
<213> ORGANISM: Mytilus galloprovincialis
<220> FEATURE:
<221> NAME/KEY: CDS
<222> LOCATION: (43)..(330)
<221> NAME/KEY: mat_peptide
<222> LOCATION: (103)..(222)
<221> NAME/KEY: sig_peptide

<222> LOCATION: (43)..(102)

<400> SEQUENCE: 1

```
aaggataata ttttgattta actgcaaact caaacgtaca at atg aag gca aca      54
                                               Met Lys Ala Thr
                                                   -20 atc ttg tta gca gtt cta gtg gca gtc ttt gtc gca ggt acg gaa gct    102
Ile Leu Leu Ala Val Leu Val Ala Val Phe Val Ala Gly Thr Glu Ala
    -15                 -10                 -5                  -1 cat tcg cac gct tgt aca tca tac tgg tgt ggt aag ttt tgt gga act    150
His Ser His Ala Cys Thr Ser Tyr Trp Cys Gly Lys Phe Cys Gly Thr
 1               5                  10                  15 gct agt tgc aca cat tat cta tgc aga gta ctc cat ccc ggt aaa atg    198
Ala Ser Cys Thr His Tyr Leu Cys Arg Val Leu His Pro Gly Lys Met
             20                  25                  30 tgc gca tgt gtt cat tgc agc agg gtg aac aat cct ttc aga gtt aat    246
Cys Ala Cys Val His Cys Ser Arg Val Asn Asn Pro Phe Arg Val Asn
         35                  40                  45 caa gtt gct aaa agt att aac gat ttg gat tac act cca ata atg aag    294
Gln Val Ala Lys Ser Ile Asn Asp Leu Asp Tyr Thr Pro Ile Met Lys
     50                  55                  60 tcg atg gaa aac ttg gac aat gga atg gat atg tta taagcaaaca         340
Ser Met Glu Asn Leu Asp Asn Gly Met Asp Met Leu
 65                  70                  75 acttatgcaa tgcagatcac aactgtgaat ctttgctatc attctcactg cttttcacct  400
ttcaacaaac gaaaaattat cagcaacttg aaaaataaca aacttgagtc atgtctgttc  460
agtttccagt ctaatattta tatcattata tgaaaggtat aacaaaatta gtaccattgt  520
gttctaatag aaacaattta taaacaagaa acattacact ttaagtataa attaacagga  580
ttttgtcctg cagctgtttt atctttcttt tctcagctat agtcttctga ttgtaataaa  640
atagcttgaa aaaaaaaaaa aaa                                          663
```

<210> SEQ ID NO 2
<211> LENGTH: 96
<212> TYPE: PRT
<213> ORGANISM: Mytilus galloprovincialis

<400> SEQUENCE: 2

```
Met Lys Ala Thr Ile Leu Leu Ala Val Leu Val Ala Val Phe Val Ala
 1               5                  10                  15

Gly Thr Glu Ala His Ser His Ala Cys Thr Ser Tyr Trp Cys Gly Lys
             20                  25                  30

Phe Cys Gly Thr Ala Ser Cys Thr His Tyr Leu Cys Arg Val Leu His
         35                  40                  45

Pro Gly Lys Met Cys Ala Cys Val His Cys Ser Arg Val Asn Asn Pro
     50                  55                  60

Phe Arg Val Asn Gln Val Ala Lys Ser Ile Asn Asp Leu Asp Tyr Thr
 65                  70                  75                  80

Pro Ile Met Lys Ser Met Glu Asn Leu Asp Asn Gly Met Asp Met Leu
                 85                  90                  95
```

<210> SEQ ID NO 3
<211> LENGTH: 681
<212> TYPE: DNA
<213> ORGANISM: Mytilus galloprovincialis
<220> FEATURE:
<221> NAME/KEY: CDS
<222> LOCATION: (13)..(300)
<221> NAME/KEY: mat_peptide

```
<222> LOCATION: (73)..(192)
<221> NAME/KEY: sig_peptide
<222> LOCATION: (13)..(72)

<400> SEQUENCE: 3
caaacgtaca ac atg aag gca aca atg ttg tta gca gtt gta gtg gct gtc      51
              Met Lys Ala Thr Met Leu Leu Ala Val Val Val Ala Val
                  -20              -15                 -10 ttt gtc gca ggt aca gaa gct cat ccg cat gtt tgc aca tcg tac tac        99
Phe Val Ala Gly Thr Glu Ala His Pro His Val Cys Thr Ser Tyr Tyr
         -5              -1   1               5 tgt agc aag ttt tgt ggg act gct ggt tgc aca cgt tat gga tgc cga       147
Cys Ser Lys Phe Cys Gly Thr Ala Gly Cys Thr Arg Tyr Gly Cys Arg
 10              15                  20                  25 aat ctc cat cgc ggg aag ctt tgc ttc tgt ctt cat tgc agc agg gtg       195
Asn Leu His Arg Gly Lys Leu Cys Phe Cys Leu His Cys Ser Arg Val
                 30                  35                  40 aag ttc ccg ttt gga gca act caa gat gct aaa agt atg aac gaa ctg       243
Lys Phe Pro Phe Gly Ala Thr Gln Asp Ala Lys Ser Met Asn Glu Leu
                 45                  50                  55 gaa tac act cca ata atg aag tcg atg gaa aat ttg gac aac gga atg       291
Glu Tyr Thr Pro Ile Met Lys Ser Met Glu Asn Leu Asp Asn Gly Met
             60                  65                  70 gat atg tta taagcaaact tatgacatga agatcacaac tgtatacttt              340
Asp Met Leu
         75 tgctattcct gtatccgctt tactcctttc ttcacacttt gtacggaatc cgtcaacaga     400 aaattcatca tcaacttgaa aactaacaaa agatgtgtcg cacacgttac actcaccagt     460 ccataagtta tatcattaaa aaaagatgaa tcaagttacc gttaacgtgt gttcagatat     520 atctctgaca gaagaagtaa ctgttaacaa gaaatactgt tttccctcaa gttattaaaa     580 attagaagtc tccctgcaac tgttttatct ttccttactc agttcttttt tcatgttcta     640 ataaaacagt ttgaaatgaa caaaaaaaaa aaaaaaaaaa a                         681

<210> SEQ ID NO 4
<211> LENGTH: 96
<212> TYPE: PRT
<213> ORGANISM: Mytilus galloprovincialis

<400> SEQUENCE: 4

Met Lys Ala Thr Met Leu Leu Ala Val Val Val Ala Val Phe Val Ala
 1               5                  10                  15

Gly Thr Glu Ala His Pro His Val Cys Thr Ser Tyr Tyr Cys Ser Lys
             20                  25                  30

Phe Cys Gly Thr Ala Gly Cys Thr Arg Tyr Gly Cys Arg Asn Leu His
         35                  40                  45

Arg Gly Lys Leu Cys Phe Cys Leu His Cys Ser Arg Val Lys Phe Pro
     50                  55                  60

Phe Gly Ala Thr Gln Asp Ala Lys Ser Met Asn Glu Leu Glu Tyr Thr
 65                  70                  75                  80

Pro Ile Met Lys Ser Met Glu Asn Leu Asp Asn Gly Met Asp Met Leu
                 85                  90                  95

<210> SEQ ID NO 5
<211> LENGTH: 40
<212> TYPE: PRT
<213> ORGANISM: Mytilus galloprovincialis
<220> FEATURE:
<221> NAME/KEY: misc_feature
```

```
<222> LOCATION: (2)..(2)
<223> OTHER INFORMATION: Xaa can be Pro or Ser
<221> NAME/KEY: misc_feature
<222> LOCATION: (4)..(4)
<223> OTHER INFORMATION: Xaa can be Val or Ala
<221> NAME/KEY: misc_feature
<222> LOCATION: (9)..(9)
<223> OTHER INFORMATION: Xaa can be Tyr or Trp
<221> NAME/KEY: misc_feature
<222> LOCATION: (11)..(18)
<223> OTHER INFORMATION: Xaa can be Ser or Gly
<221> NAME/KEY: misc_feature
<222> LOCATION: (21)..(21)
<223> OTHER INFORMATION: Xaa can be Arg or His
<221> NAME/KEY: misc_feature
<222> LOCATION: (23)..(23)
<223> OTHER INFORMATION: Xaa can be Gly or Leu
<221> NAME/KEY: misc_feature
<222> LOCATION: (26)..(26)
<223> OTHER INFORMATION: Xaa can be Asn or Val
<221> NAME/KEY: misc_feature
<222> LOCATION: (29)..(29)
<223> OTHER INFORMATION: Xaa can be Arg or Pro
<221> NAME/KEY: misc_feature
<222> LOCATION: (32)..(32)
<223> OTHER INFORMATION: Xaa can be Leu or Met
<221> NAME/KEY: misc_feature
<222> LOCATION: (34)..(34)
<223> OTHER INFORMATION: Xaa can be Phe or Ala
<221> NAME/KEY: misc_feature
<222> LOCATION: (36)..(36)
<223> OTHER INFORMATION: Xaa can be Leu or Val

<400> SEQUENCE: 5

His Xaa His Xaa Cys Thr Ser Tyr Xaa Cys Xaa Lys Phe Cys Gly Thr
 1               5                  10                  15

Ala Xaa Cys Thr Xaa Tyr Xaa Cys Arg Xaa Leu His Xaa Gly Lys Xaa
            20                  25                  30

Cys Xaa Cys Xaa His Cys Ser Arg
        35                  40

<210> SEQ ID NO 6
<211> LENGTH: 40
<212> TYPE: PRT
<213> ORGANISM: Mytilus galloprovincialis

<400> SEQUENCE: 6

His Ser His Ala Cys Thr Ser Tyr Trp Cys Gly Lys Phe Cys Gly Thr
 1               5                  10                  15

Ala Ser Cys Thr His Tyr Leu Cys Arg Val Leu His Pro Gly Lys Met
            20                  25                  30

Cys Ala Cys Val His Cys Ser Arg
        35                  40

<210> SEQ ID NO 7
<211> LENGTH: 40
<212> TYPE: PRT
<213> ORGANISM: Mytilus galloprovincialis

<400> SEQUENCE: 7

His Pro His Val Cys Thr Ser Tyr Tyr Cys Ser Lys Phe Cys Gly Thr
 1               5                  10                  15

Ala Gly Cys Thr Arg Tyr Gly Cys Arg Asn Leu His Arg Gly Lys Leu
            20                  25                  30

Cys Phe Cys Leu His Cys Ser Arg
        35                  40
```